US010927371B2

(12) United States Patent
Behr et al.

(10) Patent No.: US 10,927,371 B2
(45) Date of Patent: *Feb. 23, 2021

(54) CATIONIC SIRNAS, SYNTHESIS AND USE FOR RNA INTERFERENCE (75) Inventors: France Jean-Paul Behr, Strasbourg (FR); Mitsuharu Kotera, Strasbourg (FR); Nadege Pfender, Lispheim (FR); Jean-Serge Remy, Neugartheim (FR)

(73) Assignees: Centre National De La Recherche Scientifique (CNRS), Paris (FR); Universite De Strasbourg, Strasbourg (FR); Pollyplus Transfection, Cedex (FR)

( * ) Notice: Subject to any disclaimer, the term of this patent is extended or adjusted under 35 U.S.C. 154(b) by 1516 days.

This patent is subject to a terminal disclaimer.

(21) Appl. No.: 12/735,595

(22) PCT Filed: Jan. 30, 2009

(86) PCT No.: PCT/IB2009/050379
§ 371 (c)(1),
(2), (4) Date: Dec. 15, 2010

(87) PCT Pub. No.: WO2009/095887
PCT Pub. Date: Aug. 6, 2009

(65) Prior Publication Data
US 2011/0118331 A1    May 19, 2011

(30) Foreign Application Priority Data
Jan. 30, 2008    (FR) ...................... 08 00492

(51) Int. Cl.
C12N 15/11    (2006.01)
(52) U.S. Cl.
CPC ........ *C12N 15/111* (2013.01); *C12N 2310/14* (2013.01); *C12N 2310/351* (2013.01); *C12N 2320/32* (2013.01)
(58) Field of Classification Search
CPC .............. C12N 15/113; C12N 2310/14; C12N 15/8218; C12N 2310/11; C12N 15/111; A61K 31/713; A61K 2300/00; A61K 49/0056; C07K 2319/00
See application file for complete search history.

(56) References Cited

U.S. PATENT DOCUMENTS

| 6,071,890 | A | 6/2000 | Scheule et al. | |
| 7,772,201 | B2* | 8/2010 | Mixson | 514/44 R |
| 8,399,422 | B2 | 3/2013 | Neuberg et al. | |
| 2003/0100113 | A1 | 5/2003 | Behr et al. | |
| 2004/0019008 | A1 | 1/2004 | Lewis et al. | |
| 2004/0204377 | A1* | 10/2004 | Rana | 514/44 |
| 2006/0002991 | A1 | 1/2006 | Essler et al. | |
| 2006/0019912 | A1* | 1/2006 | Burkoth et al. | 514/44 |
| 2006/0073505 | A1* | 4/2006 | Griffey | C07H 21/02 435/6.12 |
| 2009/0069262 | A1 | 3/2009 | Behr | |
| 2009/0074852 | A1* | 3/2009 | Kaufmann et al. | 424/450 |

FOREIGN PATENT DOCUMENTS

JP        2004137143      5/2004
WO     WO 2004110499 A1 * 12/2004

OTHER PUBLICATIONS

Chiu et al., Visualizing a correlation between siRNA localization, cellular uptake, and RNAi in living cells, 2004, Chemistry & Biology, vol. 11, pp. 1165-1175.*
Lodish et al., "General Structure of Proteins, Hydrophilic Amino Acids", Molecular Cell Biology, Third edition, New York, Scientific American Books, 1995, p. 55.*
Vickers et al., Efficient reduction of target RNAs by small interfering RNA and RNase H-dependent antisense agents, 2003, The Journal of Biological Chemistry, vol. 278, pp. 7108-7118.*
Elbashir et al., Duplexes of 21-nucleotide RNAs mediate RNA interference in cultured mammalian cells, 2001, Nature, vol. 411, pp. 494-498.*
Inoue et al., Efficient delivery of siRNA using dendritic poly(L-lysine) for loss-of-function analysis, 2008, Journal of Controlled Release, vol. 126, pp. 59-66.*
Pitsch et al., Reliable chemical synthesis of oligoribonucleotides (RNA) with 2'-O-[(triisoprophylsilyl)oxy]methyl(2'-O-tom)-protected phosphoramidites, 2001, Helvetica Chimica Acta, vol. 84, pp. 3773-3795.*
International Search Report for PCT/IB2009/050379, dated Jun. 17, 2009.
Moschos et al., "Lung Delivery Studies using SIRNA Conjugated to TAT (48-60) and Penetratin Reveal Peptide Induced Reduction in Gene Expression and Induction of Innate Immunity", Bioconjugate Chemistry Sep.-Oct. 2007 vol. 18, No. 5, pp. 1450-1459.
Muratovska et al., "Conjugate for Efficient Delivery of Short Interfering RNA (SIRNA) into Mammalian Cells", FEBS Letters Jan. 30, 2004, vol. 558, No. 1-3, pp. 63-68.
Pons, Bénédicte et al., "Online Synthesis of Diblock Cationic Oligonucleoides for Enchanced Hybridization to Their Complementary Sequence", Chembiochem, vol. 7, No. 8, pp. 1173-1176, (2006).
Chen, Chang-Po et al., "A Concise Method for the Preparation of Peptide and Arginine-Rich Peptide-Conjugated Antisense Oligonucleotide", Bioconjugate Chemistry, vol. 14, No. 3, pp. 532-538, (May 2003).
Pitié, Marguerite et al., "Cleavage of Double-Stranded DNA by Manganese Tris (Methylpyridiniumyl) Porphyrin Linked to 3'-Spermine Oligonucleotides" JBIC. Journal of Biological Inorganic Chemistry, vol. 1, No. 3, pp. 239-246, (Feb. 1996).

(Continued)

Primary Examiner — Dana H Shin
(74) Attorney, Agent, or Firm — Nixon & Vanderhye, PC (57) ABSTRACT The invention relates to cationic siRNAs, characterized in that they are double-stranded RNA fragments, grafted to the ends of which are oligocations, the number of cationic charges grafted being comparable to or greater than that of the anionic charges carried by the internucleoside phosphates of the RNA strands.

23 Claims, 9 Drawing Sheets
Specification includes a Sequence Listing.

(56) References Cited

OTHER PUBLICATIONS

Sund, Christian et al., "Synthesis of C-Branched Spermine Tethered Oligo-DNA and the Thermal Stability of the Duplexes and Triplexes", Tetrahedron, vol. 52, No. 37 pp. 12275-12290, (1996).
Ching-Hsuan, Tung et al., "Polyamine-Linked Oligonucleotides for DNA Triple Helix Formation", Nucleic Acids Research, vol. 21, No. 23, pp. 5489-5494, (1993).
International Search Report for PCT/IB2006/004085, dated Feb. 11, 2008.
Written Opinion of the International Searching Authority for PCT/IB2006/004085, dated Feb. 11, 2008.
Office Action dated Dec. 13, 2011, issued in connection with U.S. Appl. No. 12/086,599.
Chen Jian-hai et al "Application of cationic polymer vector for gene delivery systems" Acta Pharmaceutica Sinica, vol. 38, No. 4, pp. 316-320 (Apr. 30, 2003).

Schmid et al, "Recognition of DNA Sequences by Strand Replacement with Polyamino-oligonucleotides", Tetrahedron Letters, vol. 36, No. 9, pp. 1447-1450, 1995.
Dias et al, "Antisense Oligonucleotides; Basic Concepts and Mechanisms", Molecular Cancer Therapeutics, Mar. 2002 1; 347 (11 pages).
Ilies et al, "Pyridinium cationic lipids in gene delivery: as in vitro and in vivo comparison of transfection efficiency versus a tetraalkylammonium congener", Archives of Biochemistry and Biophysics 435 (2005); 217-226.
Quek et al, "Synthesis and properties of N,N'-dialkylimidazolium bis(nonafluorobutane-1-sulfonyl)imides: a new subfamily of ionic liquids", Tetrahedron 62 (2006) 3137-3145.
De la Torre et al., "Synthesis and Binding Properties of Oligonucleotides Carrying Nuclear Localization Sequences", Bioconjugate Chemistry, 1999, vol. 10, pp. 1005-1012.

\* cited by examiner

Figure 1

<GL3>S$_5$ decomposed

CATIONIC SIRNAS, SYNTHESIS AND USE FOR RNA INTERFERENCE

This application is the U.S. national phase of International Application No. PCT/I62009/050379, filed 30 Jan. 2009, which designated the U.S. and claims priority to French Application No. 08/00492, filed 30 Jan. 2008, the entire contents of each of which are hereby incorporated by reference.

The invention relates to cationic siRNAs (small interfering ribonucleic acids), to their automatic synthesis and to their biological applications based on their intracellular penetration properties involving the mechanism of RNA interference.

RNA interference is an intracellular mechanism that allows the sequence-specific control of expression of an endogenous or exogenous gene. The mediators of this mechanism are small helices of bicatenary ribonucleic acid of about 2 turns, siRNAs, of identical sequence to a fragment of the target gene. Although RNA interference can result in a permanent modification of the target gene in the chromatin of a cell, the most immediate effect of the introduction of an siRNA in a cell is the inactivation of the target messenger RNA. siRNAs are generally formed from two 19-mer oligoribonucleotides of complementary sequences comprising 3'-dTdT extensions, but certain imperfect pairings or sequences of up to 27-mer may also be effective.

The disappearance of a protein or the selective destruction of a viral RNA may have therapeutic applications of major interest in fields as varied as oncology, allergy or infectious diseases. Unfortunately, intact animal cells are impermeable to nucleic acids, as shown by the unfruitful attempts to introduce siRNA per se into cells in culture or in vivo. Animal experimentation nevertheless shows that the liver, which is an organ that is capable of rapidly regenerating its cells, or muscle cells, which are particularly large and robust, can uptake siRNA and survive rupture of their cell membrane induced by the injection process. However, the rapid intravenous injection of a large volume of liquid or the very localized nature of intramuscular injection are incompatible with use in human therapy.

Transfection of siRNA into the cytoplasm of cells— without rupturing the cell membrane—may be obtained after mixing with an excess of cationic transporter. Polycationic macromolecules such as polyethyleneimine or cationic lipid aggregates are capable of performing this vector role (1). Specifically, polyanionic siRNA molecules aggregate with an excess of transporter, forming a fine cationic precipitate. These particles allow the effective transfection of siRNA into a large number of cells in culture via anionic heparan sulfates present at the surface of the cells (2).

In an animal, the same is no longer the case. When injected into the blood, the particles are taken up and digested by the cells that phagocytose the microbial particles. When injected into a tissue or a tumor, their size (100-1000 nm) prevents their diffusion towards cells located beyond the site of injection. Recent studies (3) and (4) nevertheless show that it is possible to avoid the phagocytic cells of the blood without totally inhibiting the cell binding, by covering the particles with polyethylene glycol residues (stealth particles).

These considerations led the inventors to envision the synthesis of intrinsically cationic siRNAs, i.e. modified siRNA molecules in which the cationic charges compensate for the anionic charges borne by the phosphates of the nucleic acid. These compounds might possibly dispense with a vector to enter the cell, and consequently the medicament would have the advantage of being molecular instead of particulate.

So as not to disrupt either the binding of the siRNA to the protein complex which destroys the messenger RNA, or the recognition of the latter by hybridization, chemical modifications are possible only at the ends of the nucleic acid.

A very large number of chemical units have in the past been grafted onto the ends of oligonucleotides, for the purpose of increasing their cell penetration for therapeutic purposes via antisense approaches. A number of articles very recently published report similar attempts in the field of siRNAs.

A first article published in 2006 mentions the conjugation of polyethylene glycol to an siRNA via a disulfide bridge, but the cell internalization nonetheless requires noncovalent association by mixing with a cationic polymer (5).

In 2007, two articles described the use of siRNAs (40 anionic charges) conjugated to various cationic peptides comprising 7 or 8 cationic charges. These siRNAs remain very anionic and, on the authors' own admission, the intracellular penetration and the efficacy are not increased (6) and (7).

The direct chemical grafting of a preformed polycation onto an oligonucleotide as described in the preceding articles is possible, but causes precipitation problems and may make the characterization imprecise on account of the polydispersity of the cationic polymer when it becomes a matter of manipulating polycations comprising a number of charges comparable to that of the oligonucleotide. The inventors have overcome the above problems by relying on a technique of sequential synthesis of the oligocation via conjugation chemistry identical to that used for the synthesis of the oligoribonucleotide sequence itself. The automatic synthesis of oligodeoxyribonucleotide-oligospermine conjugates was the subject of a preceding international PCT patent application (8).

Important modifications have been made to the synthesis/purification/characterization/storage of the compounds described in the preceding PCT application, since the presence of the 2'-OH group makes the synthesis more difficult and above all makes the compounds more unstable: its deprotection involves an additional step—traces of RNases degrade the RNA—the ammonium/amine functions of spermines are acid/base catalysts that bring about the hydrolysis of oligoribonucleotide-oligospermine conjugates.

The invention is thus directed toward providing intrinsically cationic siRNAs.

The invention is also directed toward a method for synthesizing these cationic siRNAs that may be extended to the industrial scale with a view to GMP production.

According to another aspect, the invention is also directed toward applications of the novel siRNAs in the pharmaceutical and biotechnological fields.

The cationic siRNAs of the invention are characterized in that they are fragments of double-stranded RNA, at the ends of which are grafted oligocations, the total number of grafted cationic charges being comparable to or greater than that of the anionic charges borne by the internucleoside phosphates of the RNA strands.

Unexpectedly, and as demonstrated by the results given in the examples, such cationic siRNAs are capable of inducing RNA interference in the absence of any transfection agent. The demonstration is made in a controlled environment, on cells in culture, in which cationic siRNA-oligopeptide conjugates that remain largely anionic showed no effect (see hereinabove).

The term "double-stranded RNA" means a double helix of nucleic acid of the A family induced by the presence of an atom other than H in position 2' of the ribose (as opposed to DNA, which is a B helix).

The overall charge Σ of the cationic siRNA, i.e. the total sum of the chemically grafted cationic charges minus the total sum of the anionic charges of the internucleoside phosphate groups, is from −30 to +50. Specifically, siRNAs (charge −40) grafted onto a TAT peptide of sequence SEQ ID No. 1 GRKKRRQRRRPPQC (charge +9; Σ=−31) or onto a penetratin peptide of the sequence SEQ ID No. 2 RQIKIWFQNRRMKWKKC (charge +8; Σ=−32) are incapable of inducing RNA interference without a vector (9).

The base complementarity of the RNA double helix may be total or partial.

In one embodiment variant, each oligoribonucleotide has a single-strand extension at the 3' end of the double helix.

In another variant, the oligocations are grafted at the 3' and/or 5' end of the sense strand and/or at the 3' end of the antisense strand, the antisense strand being that which guides the protein complex responsible for the degradation of the messenger RNA. Grafting in the 5' position of the antisense strand abolishes the RNA interference effect.

Preferably, the cationic siRNAs that are the subject of the invention are formed from double-stranded RNA fragments 15 to 30 ribonucleotides long, in particular 19 to 30 ribonucleotides long, at the ends of which are grafted, by covalent bonding, 1 to 3 oligocations, the number of cumulative cationic charges of which is comparable to or greater than the number of anionic charges borne by the RNA.

The invention is more particularly directed toward cationic siRNAs in which at least one strand corresponds to formula (I)

$$N_i\text{-}A_j \text{ or } A_j\text{-}N_i \tag{I}$$

in which
$N_i$ represents an i-mer oligoribonucleotide, with i=15 to 30 and in particular 19 to 30, and also any chemical modifications or substitutions that conserve the A form of the double helix of the siRNA,
$A_j$ represents a j-mer oligocation, with j=1 to 50, A corresponding
to formula (II)

$$-\text{HPO}_3-R^1-(X-R^2)_{n1}-X-R^3-O- \tag{II},$$

with $R^1$, $R^2$ and $R^3$, which may be identical or different, representing a lower alkylene radical, X being NH or $NC(NH_2)_2$, and n1=2 to 20, or
to formula (III)

$$-\text{HPO}_3-R^4-CH(R^5X^1)-R^6-O-, \tag{III}$$

with $R^4$, $R^5$ and $R^6$, which may be identical or different, representing a lower alkylene radical and $X^1$ being chosen from putrescine, spermidine or spermine, or
to formula (IV)

$$-\text{HPO}_3-R^7\text{-}(aa)_{n2}-R^8-O-, \tag{IV}$$

with $R^7$ and $R^8$, which may be identical or different, representing a lower alkylene radical, $(aa)_{n2}$ being a peptide containing natural amino acids with cationic side chains, such as arginine, lysine, ornithine, histidine or diaminopropionic acid and n2=2 to 20.

In the description and the claims, the term "lower alkylene radical" means a linear, branched or substituted C1-C5 alkylene radical.

In one preferred embodiment of the invention, the oligocations are oligoamines. These oligoamines are advantageously chosen from the group comprising spermine, spermidine or putrescine.

Corresponding cationic siRNAs are advantageously oligonucleotide-oligospermines of structure (V)

in which N, i and j are as defined above.

The fields of application of RNA interference are broadening. siRNAs are used by the pharmaceutical and biotechnological industry to establish a link between genes, diseases and molecules that are potentially active against these diseases; these are essentially high-throughput screening techniques on animal cells. The cationic siRNAs of the invention make it possible to simplify the screening, and above all to extend the technique to animals where physiology, biodistribution and excretion would be taken into account in the validation of a compound in the preclinical phase, thus increasing the chances of success and reducing expensive failures at the clinical phase.

However, the greatest potential of siRNAs is found in their direct use as medicaments for inhibiting the biosynthesis of an RNA or of a protein in the cells of a patient. Very diverse pathologies such as cancer, viral infections, asthma or autoimmune diseases then become curable.

The invention consequently covers the use of cationic siRNAs for these applications.

The invention is thus directed toward the cationic siRNAs defined above for a use as medicaments.

More particularly, the invention is directed toward pharmaceutical compositions characterized in that they contain an effective amount of at least one siRNA as defined above, in combination with a pharmaceutically inert vehicle.

The invention is also directed toward the application of said cationic siRNAs in molecular biology, functional genomics and in screening techniques.

The invention is also directed toward a process for the automated synthesis of a strand of cationic siRNA, characterized in that it comprises:
the sequential coupling from 3' to 5' of ribonucleotides to a solid support, preceded and/or followed by the sequential coupling of cationic synthons, the strand corresponding to formula (VI)

$$dT\text{-}dT\text{-}(N)i\text{-}Aj \text{ or } Aj\text{-}dT\text{-}dT\text{-}(N)i \tag{VI}$$

with N, i, A and j as defined above.

The invention is more particularly directed toward a process for synthesizing cationic siRNAs in which the cationic synthons are phosphoramidite oligoamines and correspond
to formula (VII)

$$P(OR^9)(N(R^{10})_2)-O-R^1-(X-R^2)_{n1}-X-R^3-O\text{-Prot}, \tag{VII}$$

in which $R^1$, $R^2$, $R^3$ and n1 are as defined above, X is a protected group NH or $NC(NH_2)_2$, $R^9$ is $-CH_2CH_2CN$ or a lower alkylene radical, $R^{10}$ is a lower alkylene radical, or $-N(R^{10})_2$ is a pyrrolidino, piperidino or morpholino radical and Prot is a protecting group used in oligonucleotide synthesis, such as DMT or MMT; or to formula (VIII)

$$P(OR^9)(N(R^{10})_2)-O-R^4-CH(R^5X1)R^6-O-Prot, \qquad (VIII)$$

in which $R^4$, $R^5$ and $R^6$, which may be identical or different, represent a lower alkylene radical, $X^1$ is a putrescine, spermidine or spermine with suitable protecting groups, and $R^9$ and $R^{10}$ are as defined above; or to formula (IX)

$$P(OR^9)(N(R^{10})_2)-O-R^7-(aa)_{n2}-R^8-O-Prot, \qquad (IX)$$

in which $R^7$, $R^8$, $R^9$, $R^{10}$, n2 and Prot are as defined above, $(aa)_{n2}$ is a peptide containing natural amino acids with protected cationic side chains, such as arginine, lysine, ornithine, histidine or diaminopropionic acid, and n2=2 to 20.

In one preferred embodiment of the invention, the oligoamine is an oligospermine.

Other characteristics and advantages of the invention are given in the examples that follow.

The characteristics of synthesis and purification of oligoribonucleotide-oligospermine conjugates and the RNA interference properties of the corresponding siRNAs are detailed in these examples, without limiting the invention to these individual compounds. In particular, the synthesis of a 21-mer that screens for luciferase and that comprises up to 30 spermine units is described. When the number of cationic charges is similar to the number of phosphates borne by the corresponding siRNA, particularly large and selective extinction of the luciferase gene is observed in a cell line that constitutively expresses this gene.

Reference will be made in the examples to FIGS. 1 to 6, which represent, respectively.

EXAMPLE 1

Synthesis, Purification and Characterization of 21-MER Oligonucleotides Comprising n Spermines, of Formula <GL3ss>$S_n$, in which <GL3ss> is a 21-mer oligonucleotide (SEQ ID NO: 3), S is a phosphospermine residue, n=0, 1, 3, 5, 20, 30.

Automated synthesis: A series of protected 21-mer oligonucleotides <GL3ss>, of sequence SEQ ID No. 3 $^3$'dTdT-AGCUUCAUGAGUCGCAUUC$^{5'}$, the ribonucleotide part of which, corresponding to nucleotides 153 to 171 of the *Photinus pyralis* luciferase gene present in the plasmid GL3 (Promega), was solid-phase synthesized using β-cyanoethyl (CE) phosphoramidite chemistry, on an Expedite synthesizer. The resin already comprised two pregrafted deoxythymidines. The synthesis was continued with n cycles using the spermine phosphoramidite synthon. The compounds having the structure below (n=0, 1, 3, 5, 20, 30), bound to the resin, were obtained.

The CE phosphoramidites, the Ultramild supports and the general reagents used for the automated synthesis are obtained from Glen Research (Eurogentec). The spermine phosphoramidite is obtained from Novalyst. The Ultramild reagents allow the deprotection of the protecting groups on the nucleic bases and the simultaneous cleavage of the oligo from the solid support under milder alkaline conditions. The monomers used, namely A protected with a phenoxyacetyl group (Pac-A-CE), G protected with a 4-isopropylphenoxy-acetyl group ((iPr-Pac)-G-CE) and C protected with an acetyl group (Ac—C-CE), prevented the degradation of the compounds during work-up. The 2'-OH position of the nucleotides was protected with the tert-butyldimethylsilyl TBDMS protecting group.

The automated synthesis was performed under standard coupling conditions, except in the case of the coupling of spermine phosphoramidite, which required a longer reaction time (20 minutes) and a more concentrated phosphoramidite solution (0.1M, i.e. 120 mg per ml of anhydrous acetonitrile). In the case of coupling 20 and 30 spermines, a double coupling reaction was required in the case of the first 4 spermines.

The fractions containing the colored dimethoxytrityl cation released at each step of the synthesis were collected, diluted and analyzed by spectrophotometry so as to determine the yields for the coupling steps. For the couplings of the four natural nucleotides (A, U, C and G), the yields exceeded 97%, whereas the yields for the coupling of the spermine phosphoramidite were between 90% and 98%.

Similarly, the following were synthesized:
a negative control sequence comprising 20 spermines SEQ ID No. 4, the sequence of which is derived from the corresponding region of luciferase of the GL2 plasmid (Promega) 3'dTdT-AGCUUCAUAAGGCG-CAUGC5'. The oligonucleotide <GL2ss>$S_{20}$ comprises 3 mismatches relative to the homogoue sequence of GL3 and, as a result, the corresponding siRNA does not have the capacity to interfere with the messenger RNA of the GL3 luciferase produced by the cells;
an antisense sequence SEQ ID No. 5 3'dTdT-GAAUGCGACUCAUGAAGCU5'comprising a 5' spermine. In this case, it is the other strand <GL3 as>$S_1$ of the double helix of siRNA that bears the cationic part.

| Mean coupling yield for the spermines | |
|---|---|
| <GL3ss>$S_1$ | 98% |
| <GL3ss>$S_3$ | 97% |
| <GL3ss>$S_5$ | 95% |
| <GL3ss>$S_{20}$ | 92% |
| <GL3ss>$S_{30}$ | 90% |
| <GL3as>$S_1$ | 98% |
| <GL2ss>$S_{20}$ | 90% |

In all cases, the DMT-ON strategy was used, conserving the DMT group in the final 5' position of the oligomers so as to facilitate the purification.

Post-synthetic treatment: After the automated synthesis, the oligomers were released from the solid support and simultaneously deprotected under the standard Ultramild conditions, by treatment with 28% aqueous ammonia at room temperature overnight.

After lyophilization, the second step consisted in deprotecting the TBDMS group in the 2'-OH position, using a 1.0 M solution of tetrabutylammonium fluoride TBAF in THF (Aldrich). The oligonucleotides were treated with 50 equivalents of TBAF per TBDMS group for 15 hours, at room temperature in the dark.

Purification: The oligonucleotides were purified using Poly-Pak II™ columns (Glen Research/Eurogentec) according to the instructions given by the supplier. The final elution was performed using an acetonitrile/water mixture (50/50) in all cases, except for the oligonucleotides comprising 20 and 30 spermines, which required the use of acetonitrile/28% aqueous ammonia diluted to 1/20 (20/80). The fractions containing the oligonucleotide were revealed by placing a drop of them onto a fluorescent thin-layer silica plate and were immediately combined and lyophilized so as to remove the solvents and to avoid degradation. A white powder was thus obtained.

The manipulation of oligoribonucleotides also required the meticulous exclusion of the sources of ribonucleases. It was thus essential to wear gloves in order to avoid contamination with the RNAses present on the hands. Sterile equipment (pipettes, Eppendorf tubes) was used, all under a laminar-flow fume cupboard.

Figure 1:
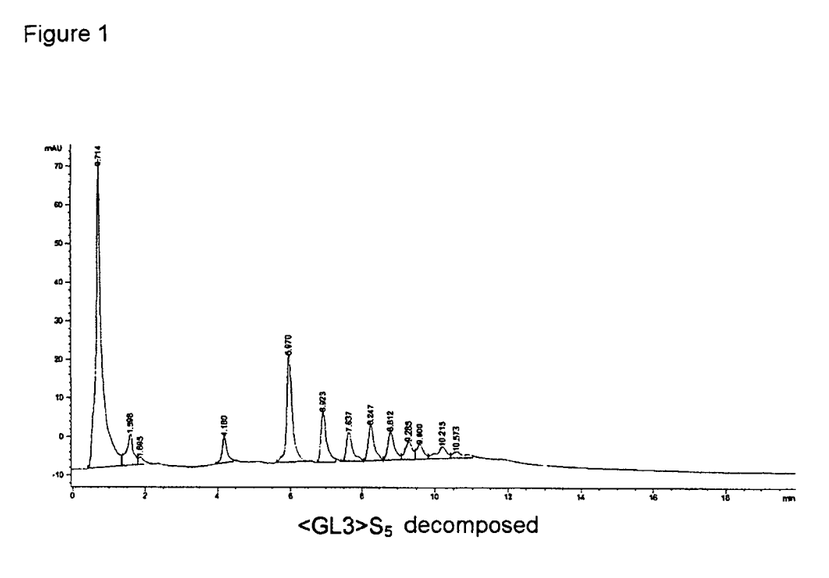
FIG. 1: HPLC analysis showing the degradation of the oligonucleotide <GL3ss>$S_5$ in water.

At the start, the RNA samples were dissolved in water and stored in a freezer. Although the unmodified strands remained stable even after several months under these conditions, HPLC analysis showed that the oligoribonucleotide-oligospermines degraded very quickly (FIG. 1, cf. HPLC conditions below).

The oligonucleotides were thus dissolved in a pH 5.6 phosphate buffer (50 mM) and stored at −20° C., which avoided degradation of the compounds by spermine-catalyzed hydrolysis, even after 3 months (HPLC monitoring).

The oligonucleotide concentration was determined using the following molar extinction coefficient (260 nm, mol$^{-1}$ dm$^3$ cm$^{-1}$):

$$\varepsilon = (15.4 N_A + 11.7 N_G + 7.4 N_C + 8.8 N_U) \times 0.9 \times 10^3$$

Figure 2:
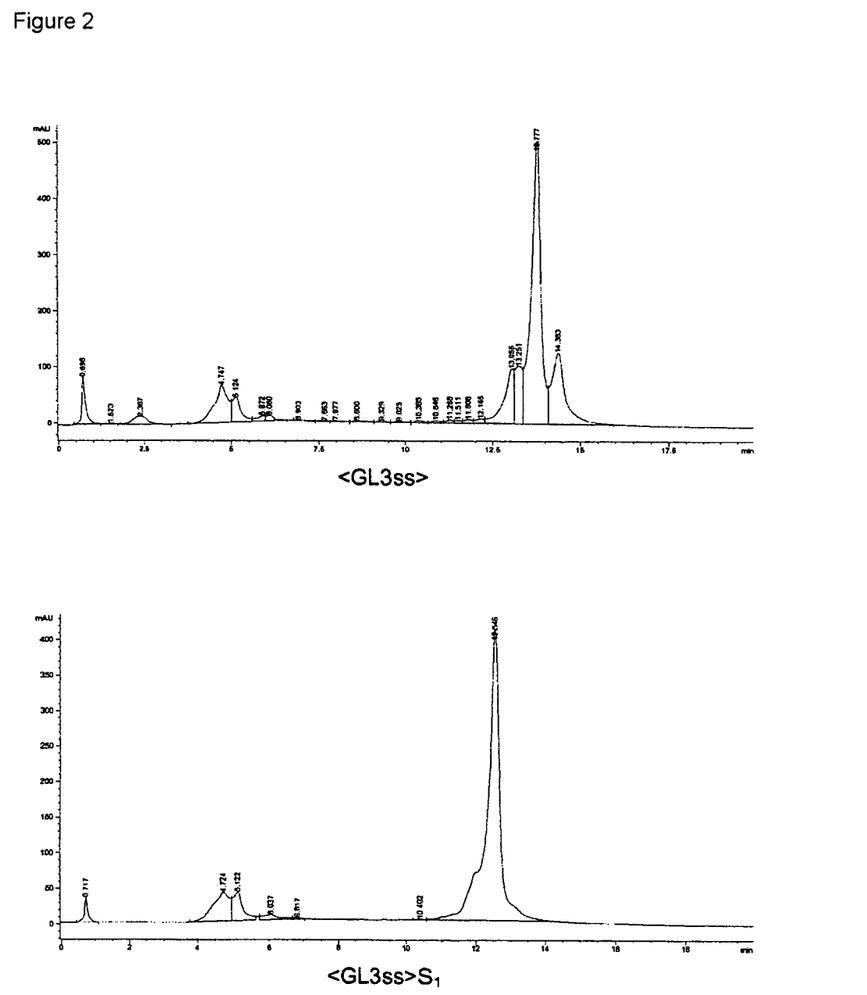
FIG. 2: HPLC profile of the oligonucleotides <GL3ss>$S_n$, with n=0, 1, 3, 5, and <GL3 as>$S_n$, with n=0, 1.

The oligonucleotides of negative overall charge comprising, respectively, 0, 1, 3 and 5 spermines were analyzed by anion-exchange HPLC (Macherey Nagel SAX 1000-8) with a linear gradient of B ranging from 0 to 100% over 15 minutes (A: KH$_2$PO$_4$ 20 mM, AcCN 20%; B: A, 1M NaCl). The HPLC profiles are shown in FIG. 2.

Figure 3:
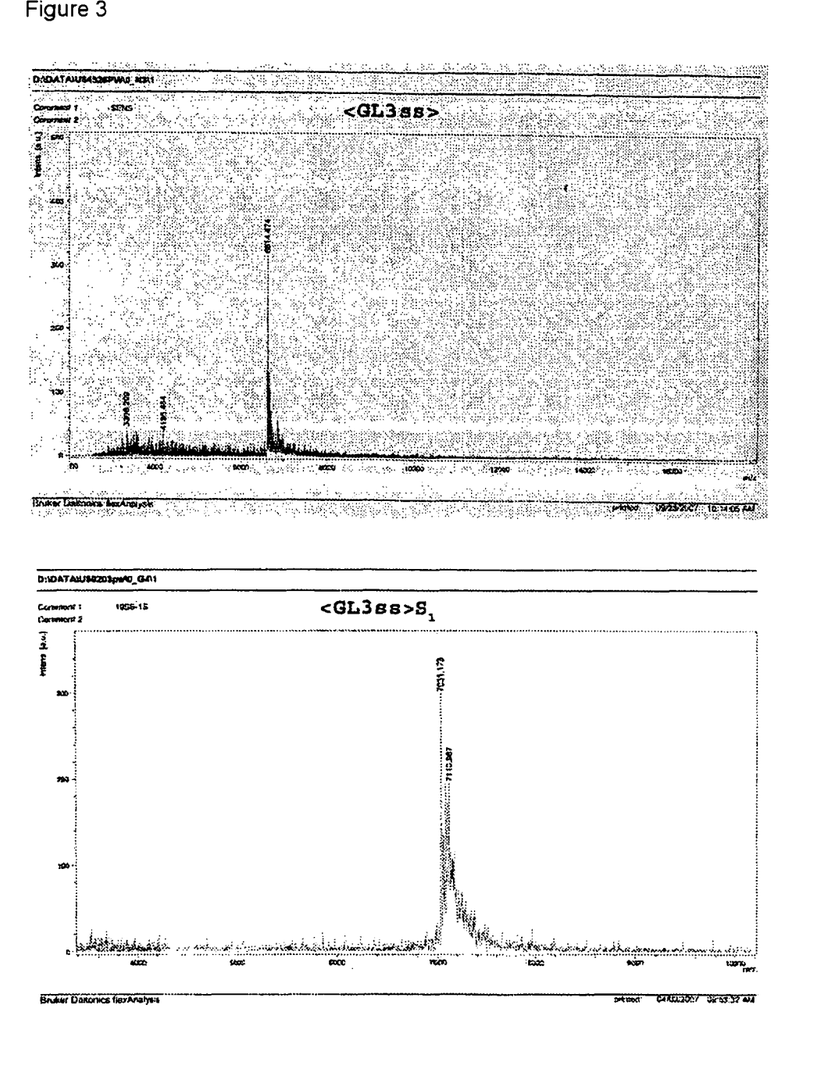
FIG. 3: MALDI-TOF mass spectra.

The oligonucleotides were dissolved in 500 μl of distilled water. The sample and the β-hydroxypyruvic acid matrix were mixed together on the plate. Once crystallized, the sample was analyzed on a Bruker Ultrafex machine. The mass spectra are given in FIG. 3.

| | Expected mass (g/mol) | Observed mass |
|---|---|---|
| <GL3ss> | 6606.9 | 6612.2 |
| <GL3ss>$S_1$ | 7015.5 | 7031.2 |
| <GL3ss>$S_3$ | 7832.5 | 7857.9 |
| <GL3 as> | 6693.9 | 6740.2 |
| <GL3 as>$S_1$ | 7101.6 | 7119.5 |
| <GL2 ss> | 6669.0 | 6678.2 |

EXAMPLE 2

RNA Interference; Extinction of the Luciferase Gene with the Cationic siRNAs. Effect of the Number of Cationic Charges Cell culture: The cell line A549Luc is obtained from human bronchial epithelial cells (CCL-185, ATCC) by stable transfection of the plasmid pGL3 (Promega).

The A549Luc cells were cultured in whole RPMI 1640 medium (Eurobio) supplemented with 10% fetal calf serum (FCS, Perbio), 2 mM of glutamax (Eurobio), 100 U/ml of penicillin (Eurobio) and 100 µg/ml of streptomycin (Eurobio) and incubated at 37° C. and 5% $CO_2$ in a moisture-saturated atmosphere.

One day before the transfection of the siRNAs, the cells were detached with trypsin (Eurobio) and resuspended in RPMI/FCS medium, to which were added 16 µl/ml of antibiotic G-418 (Promega). 24-well plates were prepared with 25 000 cells per well in 1 ml of whole medium.

Formation of the duplex siRNAs and incubation with the cells: First, the duplex siRNAs were prepared by equimolar mixing of their two complementary strands, hybridization by heating to 70° C. and cooling. The concentrations were adjusted to final concentrations on the cells of 1, 10 or 100 nM. The duplexes formed were then diluted in 100 µl of RPMI medium.

The positive control for penetration of the siRNAs into the cells was performed using the lipid transfection agent INTERFERin (Polyplus-transfection) used according to the manufacturer's recommendations. INTERFERin (2 µl) was added to the siRNA. The mixture was immediately homogenized and left to stand for 10 minutes at room temperature to promote the formation of the complexes.

During this time, the cell culture medium was aspirated and the adherent cells were washed with phosphate buffer (PBS). Next, 500 µl of RPMI were added to each well.

The duplex siRNAs (or siRNA/INTERFERin) were added to the cells (100 µl/well). The plate was homogenized by manual rotation. Each condition was performed in triplicate.

The plate was incubated at 37° C. and 5% $CO_2$ for 4 hours. After this time, the cells were observed under a microscope to check for the absence of toxicity and 500 µl of RPMI supplemented with 20% FCS were added to each well.

The plate was incubated in an oven at 37° C. and 5% $CO_2$ for 48 hours.

Measurement of the luciferase gene expression: After 48 hours, the cells were washed with PBS and then lyzed using a commercial stock solution diluted 5× (Promega). The plate was then incubated for 30 minutes at room temperature. The solutions were recovered in microtubes and centrifuged for 5 minutes at 1400 rpm at 4° C.

10 µl of each sample were deposited on a 96-well plate. The plate was analyzed using a luminometer (Mediators PhL or Berthold Centro LB690). For each sample, the light emitted by the reaction catalyzed with the luciferase protein was measured and normalized over a period of 10 s.

Assay of the total cell protein: A BSA (bovine serum albumin) range was prepared beforehand to serve as calibration. 15 µl of lysis buffer were added per tube. 15 µl of each sample to be analyzed were introduced into tubes. Three blanks formed from 15 µl of lysis buffer each were prepared. 1 ml of BCA (bicinchoninic acid) mix solution was added to each tube. The mixtures obtained were then placed in a water bath at 60° C. for 30 minutes. The absorbance was read at 562 nm.

Evaluation of the extinction of the luciferase gene: The results were first expressed in RLU (Relative Light Units) integrated over 10 seconds, normalized per milligram of protein of the cell lyzate. The efficacy of extinction of the gene in each condition was then expressed as a percentage of the expression of luciferase in cells not incubated in the presence of siRNA. Each bar represents the average value of the percentage of expression of the luciferase gene and its standard deviation.

Figure 4:
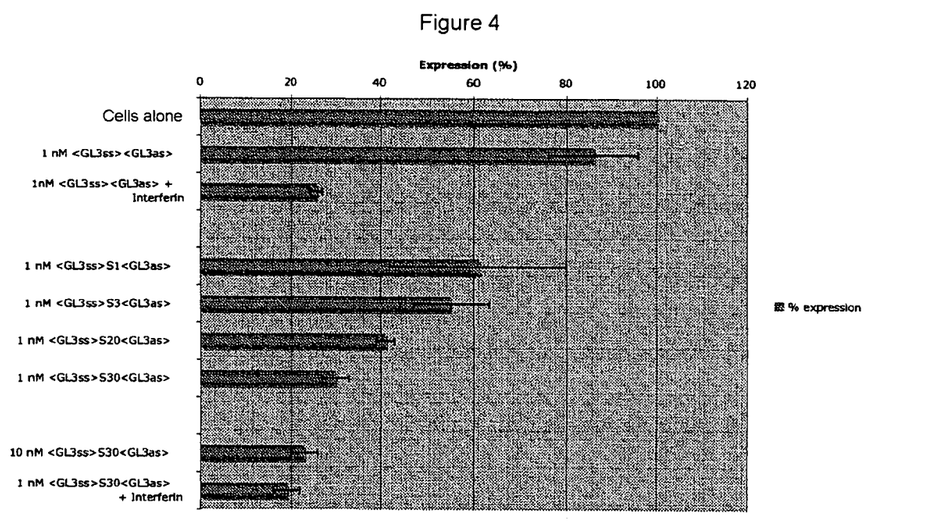
FIG. 4: Extinction of the luciferase gene as a function of the number of spermines.

From top to bottom, FIG. 4 successively shows that the siRNA <GL3ss><GL3 as> formed from the sense (ss) and antisense (as) strands of the sequence of luciferase GL3 is not active;

this same siRNA extinguishes the expression of luciferase when it is vectorized by the cationic lipid INTERFERin;

the introduction of 1-3 spermines into the molecule has little effect on luciferase expression;

the introduction of 20-30 spermines into the siRNA leads to an extinction comparable to that obtained using the INTERFERin vector;

the efficacy of siRNA with 30 spermines increases further by a factor of around 10 in combination with a lipid vehicle.

It is quite remarkable that these effects are observed at a nanomolar concentration, i.e. 10 000 times less than that used in the experiments performed with the peptides TAT and penetratin (9).

EXAMPLE 3

Figure 5:
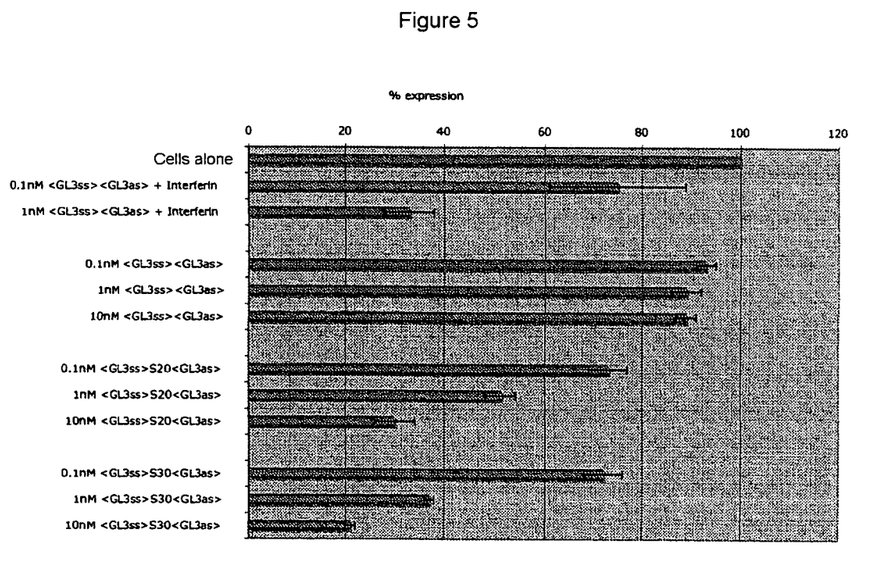
FIG. 5: Extinction of the luciferase gene as a function of the siRNA concentration.

RNA Interference; Extinction of the Luciferase Gene with Cationic siRNAs. Effect of the Concentration FIG. 5 shows from top to bottom:

the controls of siRNA without spermine vectorized by INTERFERin showing an effect at 1 nM;

the expression of the luciferase GL3 is not reduced when the cells are incubated with siRNA without grafted spermine and without INTERFERin, irrespective of the concentration;

a concentration-dependent decrease in luciferase in the presence of siRNAs comprising 20 and 30 spermines.

EXAMPLE 4

RNA Interference; Extinction of the Luciferase Gene with Cationic siRNAs. Validation Experiments FIG. 6 validates the claims and the specificity of the RNA interference.

Figure 6:
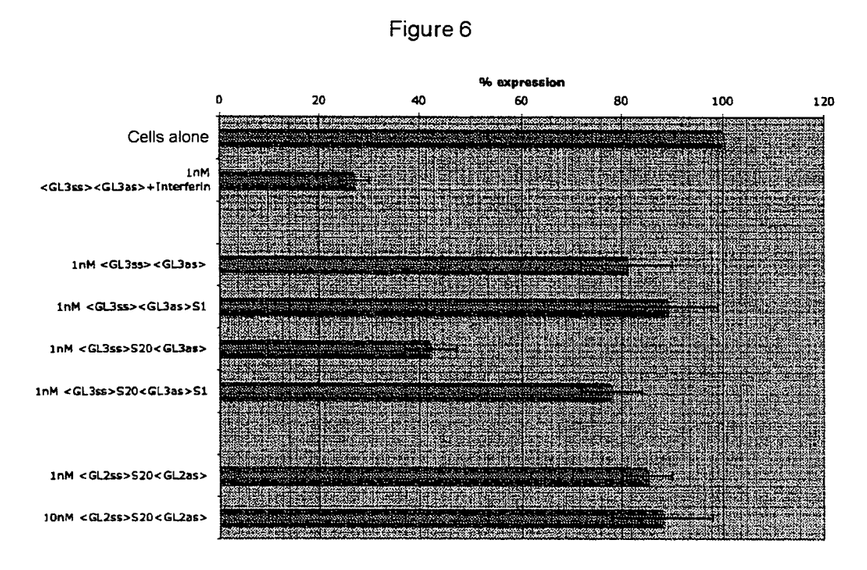
FIG. 6: Specificity controls.

After the negative controls (100% expression of the cells alone) and positive controls (27% expression of luciferase GL3 in the presence of the siRNA of sequence GL3 vectorized by INTERFERin), the siRNA <GL3ss><GLS3 as>$S_1$ this time comprising a spermine grafted in the 5' position of the antisense strand was tested.

Bars 3 to 6 show that the grafting of spermine into position 5' of the antisense strand makes the luciferase extinction effect disappear. Specifically, it is known that this position of siRNA must be phosphorylated beforehand by the cell in order to show RNA interference.

Bars 7 and 8 show that, even at a concentration 10 times higher, siRNA GL2 with 20 spermines, comprising 3 mismatches relative to the target GL3, does not reduce the expression of luciferase GL3.

BIBLIOGRAPHIC REFERENCES

1—BOLCATO-BELLEMIN, A. L., BONNET, M. E., CREUSAT, G., ERBACHER, P., and BEHR, J. P. (2007).

Sticky overhangs enhance siRNA-mediated gene silencing. Proc Natl Acad Sci USA 104, 16050-16055
2—KOPATZ, I., REMY, J. S., and BEHR, J. P. (2004). A model for non-viral gene delivery: through syndecan adhesion molecules and powered by actin. J Gene Med 6, 769-776
3—ZIMMERMANN, T. S., LEE, A. C., AKINC, A., BRAMLAGE, B., BUMCROT, D., FEDORUK, M. N., HARBORTH, J., HEYES, J. A., JEFFS, L. B., JOHN, M., JUDGE, A. D., LAM, K., MCCLINTOCK, K., NECHEV, L. V., PALMER, L. R., RACIE, T., ROHL, I., SEIFFERT, S., SHANMUGAM, S., SOOD, V., SOUTSCHEK, J., TOUDJARSKA, I., WHEAT, A. J., YAWORSKI, E., ZEDALIS, W., KOTELIANSKY, V., MANOHARAN, M., VORNLOCHER, H. P., and MACLACHLAN, I. (2006). RNAi-mediated gene silencing in non-human primates. Nature 441, 111-114
4—SANTEL, A., ALEKU, M., KEIL, O., ENDRUSCHAT, J., ESCHE, V., FISCH, G., DAMES, S., LOFFLER, K., FECHTNER, M., ARNOLD, W., GIESE, K., KLIPPEL, A., and KAUFMANN, J. (2006). A novel siRNA-lipoplex technology for RNA interference in the mouse vascular endothelium. Gene Ther 13, 1222-1234
5—KIM, S. H., JEONG, J. H., LEE, S. H., KIM, S. W., and PARK, T. G. (2006). PEG conjugated VEGF siRNA for anti-angiogenic gene therapy. Journal of Controlled Release 116, 123-129
6—MOSCHOS, S. A., WILLIAMS, A. E., and LINDSAY, M. A. (2007). Cell-penetrating-peptide-mediated siRNA lung delivery. Biochemical Society Transactions 35, 807-810
7—TURNER, J. J., JONES, S., FABANI, M. M., IVANOVA, G., ARZUMANOV, A. A., and GAIT, M. J. (2007). RNA targeting with peptide conjugates of oligonucleotides, siRNA and PNA. Blood Cells, Molecules, and Diseases 38, 1-7
8—Patent application PCT/IB2006/004085; WO2007/069092; inventors: J. P. Behr, M. Kotera, B. Pons, E. Voirin, and J. S. Remy
9—MOSCHOS, S. A., JONES, S. W., PERRY, M. M., WILLIAMS, A. E., ERJEFALT, J. S., TURNER, J. J., BARNES, P. J., SPROAT, B. S., GAIT, M. J., and LINDSAY, M. A. (2007). Lung delivery studies using siRNA conjugated to TAT(48-60) and penetratin reveal peptide induced reduction in gene expression and induction of innate immunity. Bioconjug Chem 18, 1450-1459

The invention claimed is:

1. A cationic siRNA comprising a fragment having 15 to 30 ribonucleotides of double-stranded RNA at the ends of which are grafted via a phosphate group on a ribonucleotide on the siRNA by covalent bonding 20 to 30 linear oligocations, the number of grafted cationic charges being greater than that of the anionic charges borne by the internucleoside phosphates of the RNA strands and wherein the cationic siRNA is a molecule and active at a concentration of 1 nM to 10 nM without any transfection agent.

2. The cationic siRNA according to claim 1, wherein the strand complementarity is total or partial in the double helix.

3. The cationic siRNA according to claim 1, wherein the oligocations are grafted at the 3' and/or 5' end of the sense strand and/or at the 3' end of the antisense strand.

4. The cationic siRNA according to claim 1, wherein said fragment has 19 to 30 ribonucleotides in the double-stranded RNA, at the ends of which are grafted by covalent bonding 20 to 30 linear oligocations, the total number of cationic charges being greater than the number of anionic charges borne by the RNA.

5. The cationic siRNA according to claim 1, comprising a fragment of double-stranded RNA, at the ends of which are grafted by covalent bonding oligocations, wherein at least one strand of said fragment of double-stranded RNA comprises formula (I)

$$N_i\text{-}A_j \text{ or } A_j\text{-}N_i \qquad (I)$$

in which $N_i$ represents an i-mer oligoribonucleotide, with i=15 to 30 or i=19 to 30 and any chemical modifications or substitutions that conserve the A form of a double helix of the siRNA, $A_j$ represents a j-mer oligocation, with j=20 to 30, A comprising formula (II):

$$-\text{HPO}_3-R^1-(X-R^2)_{n1}-X-R^3-O- \qquad (II),$$

with $R^1$, $R^2$ and $R^3$, which may be identical or different, represent a linear, branched or substituted C1 to C5 alkylene radical, X being NH or NC(NH$_2$)$_2$ and n1=2 to 20, or A comprising formula (III):

$$-\text{HPO}_3-R^4-CH(R^5X^1)-R^6-O-, \qquad (III)$$

with $R^4$, $R^5$ and $R^6$, which may be identical or different, representing a lower alkylene radical and $X^1$, being chosen from putrescine, spermidine or spermine, or A comprising formula (IV):

$$-\text{HPO}_3-R^7\text{-}(aa)_{n2}-R^8-O-, \qquad (IV)$$

with $R^7$ and $R^8$, which may be identical or different, representing a lower alkylene radical, $(aa)_{n2}$ being a peptide containing natural amino acids with cationic side chains of arginine, lysine, ornithine, histidine or diaminopropionic acid and n2=2 to 20.

6. The cationic siRNA according to claim 5, wherein said oligocation is a spermine, spermidine or putrescine and the ribonucleotides are 15 to 30 nucleotides long.

7. The cationic siRNA according to claim 1, wherein said cationic siRNA is an oligonucleotide-oligospermine having the structure:

$$(N)_i-[PO_3^- -(CH_2)_4-\overset{+}{N}H_2-(CH_2)_3-\overset{+}{N}H_2-(CH_2)_4-\overset{+}{N}H_2-(CH_2)_3-\overset{+}{N}H_2-(CH_2)_4-O]_jH \qquad (V)$$

wherein $N_i$ represents an i-mer oligoribonucleotide with i is 15 to 30 or i is 19 to 30 and any chemical modifications or substitutions that conserve an A form of a double helix of the cationic siRNA and j=20 to 30.

8. A pharmaceutical composition comprising, an effective amount of at least one cationic siRNA, according to claim 1, in combination with a pharmaceutically inert vehicle, a cationic lipid or a cationic polymer.

9. A process for the automated synthesis of a strand of cationic siRNA comprising:

(i) sequentially coupling from 3' to 5,' 15 to 30 ribonucleotides to a solid support, preceded and/or followed by the sequential coupling of cationic synthons, the strand comprising formula (VI):

$$dT\text{-}dT\text{-}(N)i\text{-}Aj \text{ or } Aj\text{-}dT\text{-}dT\text{-}(N)i \quad (VI)$$

wherein Ni represents an i-mer oligoribonucleotide, with i=15 to 30 or i=19 to 30, and any chemical modifications or substitutions that conserve the A form of the double helix of the siRNA, Aj represents a j-mer oligocation, with j=20 to 30, A corresponding to formula (II):

$$-\text{HPO}_3-R^1-(X-R^2)_{n1}-X-R^3-O- \quad (II),$$

with $R^1$, $R^2$ and $R^3$, which may be identical or different, represent a linear, branched or substituted C1 to C5 alkylene radical, X being NH or $NC(NH_2)_2$ and n1=2 to 20, or comprising formula (III):

$$-\text{HPO}_3-R^4-CH(R^5X^1)-R^6-O-, \quad (III)$$

with $R^4$, $R^5$ and $R^6$, which may be identical or different, representing represent a linear, branched or substituted C1 to C5 alkylene radical and $X^1$ being chosen from putrescine, spermidine or spermine;

or comprising formula (IV):

$$-\text{HPO}_3-R^7-(aa)_{n2}-R^8-O-, \quad (IV)$$

with $R^7$ and $R^8$, which may be identical or different, representing a linear, branched or substituted C1 to C5 alkylene radical, $(aa)_{n2}$ being a peptide containing natural amino acids with cationic side chains, selected from the group consisting of arginine, lysine, ornithine, histidine and diaminopropionic acid and n2=2 to 20;

wherein a 2'-OH position of the oligonucleotides is protected with a tert-butyldimethylsilyl protecting group; and (ii) deprotecting the tert-butyldimethylsilyl protecting group in the 2'—OH position.

10. The process according to claim 9, wherein the cationic synthons are phosphoramidite oligoamines and comprise formula (VII):

$$P(OR^9)(N(R^{10})_2)-O-R^1-(X-R^2)_{n1}-X-R^3-O\text{-Prot,} \quad (VII)$$

in which $R^1$, $R^2$ and $R^3$, which may be identical or different, represent a linear, branched or substituted C1 to C5 alkylene radical, and n1=2 to 20, X is a protected group NH or $NC(NH_2)_2$, $R^9$ is $-CH_2CH_2CN$ or a linear, branched or substituted C1 to C5 alkylene radical, $R^{10}$ is a lower alkylene radical or $-N(R^{10})_2$ is a pyrrolidino, piperidino, or morpholino radical and Prot is a protecting group used in oligonucleotide synthesis selected from the group consisting of dimethoxytrityl (DMT) and monomethoxytrityl (MMT);

or comprise formula (VIII):

$$P(OR^9)(N(R^{10})_2)-O-R^4-CH(R^5X^1)R^6-O\text{-Prot,} \quad (VIII)$$

with $R^4$, $R^5$ and $R^6$, which may be identical or different, representing a linear, branched or substituted C1 to C5 alkylene radical and $X^1$ being chosen from putrescine, spermidine or spermine with suitable protecting groups and $R^9$ is $-CH_2CH_2CN$ or a linear, branched or substituted C1 to C5 alkylene radical, $R^{10}$ is a linear, branched or substituted C1 to C5 alkylene radical or $-N(R^{10})_2$ is a pyrrolidino, piperidino, or morpholino radical;

or comprise formula (IX):

$$P(OR^9)(N(R^{10})_2)-O-R^7-(aa)_{n2}-R^8-O\text{-Prot,} \quad (IX)$$

in which $R^7$ and $R^8$, which may be identical or different, represent a linear, branched or substituted C1 to C5 alkylene radical, $(aa)_{n2}$ is a peptide containing natural amino acids with cationic side chains, selected from the group of arginine, lysine, ornithine, histidine and diaminopropionic acid and n2=2 to 20, $R^9$ is $-CH_2CH_2CN$ or a lower alkylene radical, $R^{10}$ is a linear, branched or substituted C1 to C5 alkylene radical or $-N(R^{10})_2$ is a pyrrolidino, piperidino, or morpholino radical and Prot is a protecting group used in oligonucleotide synthesis, selected from the group consisting of dimethoxytrityl (DMT) and monomethoxytrityl (MMT).

11. The process according to claim 10, wherein tert-butyldimethylsilyl protecting group in the 2'-OH position of the oligonucleotides is deprotected with tetrabutylammonium fluoride (TBAF) in tetrahydrofuran.

12. The process according to claim 10, wherein a 1.0 M solution of tetrabutylammonium fluoride (TBAF) is used.

13. The process according to claim 11, wherein the oligonucleotides are treated with 50 equivalents of tetrabutylammonium fluoride (TBAF) per tert-butyldimethylsilyl protecting group.

14. The process according to claim 13, wherein the oligonucleotides are treated for 15 hours.

15. The process according to claim 13, wherein the oligonucleotides are treated at room temperature and in the dark.

16. A process for preventing the hydrolysis of oligonucleotide-oligospermine conjugates, said process comprising:

(i) sequentially coupling from 3' to 5,' 19 to 30 ribonucleotides to a solid support, preceded and/or followed by the sequential coupling of cationic synthons, the strand comprising formula (VI):

$$dT\text{-}dT\text{-}(N)i\text{-}Aj \text{ or } Aj\text{-}dT\text{-}dT\text{-}(N)i \quad (VI)$$

wherein Ni represents an i-mer oligoribonucleotide, with i=15 to 30 or i=19 to 30, and any chemical modifications or substitutions that conserve the A form of the double helix of the siRNA, Aj represents a j-mer oligocation, with j=20 to 30, A corresponding to formula (II):

$$-\text{HPO}_3-R^1-(X-R^2)_{n1}-X-R^3-O- \quad (II),$$

with $R^1$, $R^2$ and $R^3$, which may be identical or different, represent a linear, branched or substituted C1 to C5 alkylene radical, X being NH or $NC(NH_2)_2$ and n1=2 to 20, or comprising formula (III):

$$-\text{HPO}_3-R^4-CH(R^5X^1)-R^6-O-, \quad (III)$$

with $R^4$, $R^5$ and $R^6$, which may be identical or different, representing a linear, branched or substituted C1 to C5 alkylene radical and $X^1$ being chosen from putrescine, spermidine or spermine;

or comprising formula (IV):

$$-\text{HPO}_3-R^7-(aa)_{n2}-R^8-O-, \quad (IV)$$

with $R^7$ and $R^8$, which may be identical or different, representing a linear, branched or substituted C1 to C5 alkylene radical, $(aa)_{n2}$ being a peptide containing natural amino acids with cationic side chains, selected from the group consisting of arginine, lysine, ornithine, histidine and diaminopropionic acid and n2=2 to 20;

wherein a 2'-OH position of the oligonucleotides is protected with a tert-butyldimethylsilyl protecting group; and

(ii) deprotecting the tert-butyldimethylsilyl protecting group in the 2'-OH position.

17. The process according to claim 16, wherein the cationic synthons are phosphoramidite oligoamines and comprise formula (VII):

$$P(OR^9)(N(R^{10})_2)-O-R^1-(X-R^2)_{n1}-X-R^3-O-Prot, \quad (VII)$$

in which $R^1$, $R^2$ and $R^3$, which may be identical or different, represent a linear, branched or substituted C1 to C5 alkylene radical, and n1=2 to 20, X is a protected group NH or NC(NH$_2$)$_2$, $R^9$ is —CH$_2$CH$_2$CN or a linear, branched or substituted C1 to C5 alkylene radical, $R^{10}$ is a lower alkylene radical or —N(R$^{10}$)$_2$ is a pyrrolidino, piperidino, or morpholino radical and Prot is a protecting group used in oligonucleotide synthesis selected from the group consisting of dimethoxytrityl (DMT) and monomethoxytrityl (MMT);

or comprise formula (VIII):

$$P(OR^9)(N(R^{10})_2)-O-R^4-CH(R^5X^1)R^6-O-Prot, \quad (VIII)$$

with $R^4$, $R^5$ and $R^6$, which may be identical or different, representing a linear, branched or substituted C1 to C5 alkylene radical and $X^1$ being chosen from putrescine, spermidine or spermine with suitable protecting groups and $R^9$ is —CH$_2$CH$_2$CN or a linear, branched or substituted C1 to C5 alkylene radical, $R^{10}$ is a linear, branched or substituted C1 to C5 alkylene radical or —N(R$^{10}$)$_2$ is a pyrrolidino, piperidino, or morpholino radical;

or comprise formula (IX):)

$$P(OR^9)(N(R^{10})_2)-O-R^7-(aa)_{n2}-R^8-O-Prot, \quad (IX)$$

in which $R^7$ and $R^8$, which may be identical or different, represent a linear, branched or substituted C1 to C5 alkylene radical, $(aa)_{n2}$ is a peptide containing natural amino acids with cationic side chains, selected from the group of arginine, lysine, ornithine, histidine and diaminopropionic acid and n2=2 to 20, $R^9$ is —CH$_2$CH$_2$CN or a linear, branched or substituted C1 to C5 alkylene radical, $R^{10}$ is a lower alkylene radical or —N(R$^{10}$)$_2$ is a pyrrolidino, piperidino, or morpholino radical and Prot is a protecting group used in oligonucleotide synthesis, selected from the group consisting of dimethoxytrityl (DMT) and monomethoxytrityl (MMT).

18. The process according to claim 16, wherein tert-butyldimethylsilyl protecting group in the 2'-OH position of the oligonucleotides is deprotected with tetrabutylammonium fluoride (TBAF) in tetrahydrofuran.

19. The process according to claim 18, wherein a 1.0 M solution of tetrabutylammonium fluoride (TBAF) is used.

20. The process according to claim 18, wherein the oligonucleotides are treated with 50 equivalents of tetrabutylammonium fluoride (TBAF) per tert-butyldimethylsilyl protecting group.

21. The process according to claim 18, wherein the oligonucleotides are treated for 15 hours.

22. The process according to claim 18, wherein the oligonucleotides are treated at room temperature and in the dark.

23. A cationic siRNA comprising a fragment of double-stranded RNA at the ends of which are grafted via a phosphate group on a ribonucleotide on the siRNA by covalent bonding oligocations, wherein said oligocations are selected from the group consisting of putrescine, spermidine and spermine and wherein 20 to 30 oligocations are grafted, wherein each oligonucleotide has a single-strand extension at the 3' end of the double helix and the oligocations are grafted at the 3' and/or 5' end of the sense strand or at the 3' end of the antisense strand wherein the cationic siRNA is a molecule and active at a concentration of 1 nM to 10 nM without any transfection agent.

* * * * *

SEQUENCE LISTING

<160> NUMBER OF SEQ ID NOS: 5

<210> SEQ ID NO 1
<211> LENGTH: 14
<212> TYPE: PRT
<213> ORGANISM: Human immunodeficiency virus

<400> SEQUENCE: 1

Gly Arg Lys Lys Arg Arg Gln Arg Arg Arg Pro Pro Gln Cys
1               5                   10

<210> SEQ ID NO 2
<211> LENGTH: 17
<212> TYPE: PRT
<213> ORGANISM: Unknown
<220> FEATURE:
<223> OTHER INFORMATION: Description of Unknown: penetratin peptide

<400> SEQUENCE: 2

Arg Gln Ile Lys Ile Trp Phe Gln Asn Arg Arg Met Lys Trp Lys Lys
1               5                   10                  15

Cys

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
cuuacgcuga guacuucgat t                                              21

<210> SEQ ID NO 4
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
cguacgcgga auacuucgat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ucgaaguacu cagcguaagt t                                              21
```

UNITED STATES PATENT AND TRADEMARK OFFICE
CERTIFICATE OF CORRECTION

PATENT NO. : 10,927,371 B2
APPLICATION NO. : 12/735595
DATED : February 23, 2021
INVENTOR(S) : Behr et al.

Page 1 of 1

It is certified that error appears in the above-identified patent and that said Letters Patent is hereby corrected as shown below:

On the Title Page

Item (73) Assignees: Please change the name of the third Assignee from "Pollyplus Transfection" to --Polyplus Transfection--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*